(12) United States Patent
Giese et al.

(10) Patent No.: US 12,350,038 B2
(45) Date of Patent: Jul. 8, 2025

(54) METHOD FOR DETERMINING THE AUDITORY THRESHOLD OF A TEST SUBJECT, HEARING AID SYSTEM, METHOD FOR SETTING HEARING AID PARAMETERS AND COMPUTER READABLE MEDIUM FOR PERFORMING THE METHOD

(71) Applicant: Sivantos Pte. Ltd., Singapore (SG)

(72) Inventors: Ulrich Giese, Fuerth (DE); Eva Droste, Erlangen (DE)

(73) Assignee: Sivantos Pte. Ltd., Singapore (SG)

( * ) Notice: Subject to any disclaimer, the term of this patent is extended or adjusted under 35 U.S.C. 154(b) by 757 days.

(21) Appl. No.: 17/118,968

(22) Filed: Dec. 11, 2020

(65) Prior Publication Data
US 2021/0177309 A1 Jun. 17, 2021

(30) Foreign Application Priority Data
Dec. 11, 2019 (DE) .......................... 102019219385.4

(51) Int. Cl.
*A61B 5/12* (2006.01)
*A61B 5/00* (2006.01)

(52) U.S. Cl.
CPC .............. *A61B 5/12* (2013.01); *A61B 5/6815* (2013.01)

(58) Field of Classification Search
None
See application file for complete search history.

(56) References Cited

U.S. PATENT DOCUMENTS

| 6,350,243 B1 | 2/2002 | Johnson |
| 2010/0254538 A1 | 10/2010 | Latzel |
| 2010/0303269 A1 | 12/2010 | Baechler |
| 2011/0105967 A1* | 5/2011 | Zeng ...................... A61M 21/00 607/57 |
| 2011/0313315 A1* | 12/2011 | Attias ...................... G16Z 99/00 600/559 |
| 2013/0266163 A1* | 10/2013 | Morikawa ............ A61B 5/6803 381/312 |

OTHER PUBLICATIONS

Schlittenlacher, Josef et al.: "Audiogram estimation using Bayesian active learning", The Journal of Acoustical Society America, American Institute of Physics for the Acoustical Society of America, New York, NY, USA, vol. 144, No. 1, Jul. 27, 2018 (Jul. 27, 2018), pp. 421-430, XP012230342.
Extended European Search Report, dated Apr. 14, 2021 and English translation of the relevant pages.

* cited by examiner

*Primary Examiner* — Aurelie H Tu
(74) *Attorney, Agent, or Firm* — Laurence A. Greenberg; Werner H. Stemer; Ralph E. Locher

(57) ABSTRACT

To determine an auditory threshold of a test subject, according to the method, multiple tone sets, which predominantly contain a plurality of noises, having properties remaining uniform within a tone set, are presented in succession to a test subject by use of an output transducer. The test subject is asked to indicate a perceived number of noises from the presented tone set after each presentation of one of these tone sets. As a function of the perceived number of noises, a property of at least one part of the noises is changed in relation to the preceding tone set for the presentation of a following tone set and the following tone set is presented to the test subject. As a function of the respective perceived number of noises in the presented tone sets, at least one value of the auditory threshold of the test subject is estimated.

15 Claims, 1 Drawing Sheet

METHOD FOR DETERMINING THE AUDITORY THRESHOLD OF A TEST SUBJECT, HEARING AID SYSTEM, METHOD FOR SETTING HEARING AID PARAMETERS AND COMPUTER READABLE MEDIUM FOR PERFORMING THE METHOD

CROSS-REFERENCE TO RELATED APPLICATION

This application claims the priority, under 35 U.S.C. § 119, of German Patent Application DE 10 2019 219 385.4, filed Dec. 11, 2019; the prior application is herewith incorporated by reference in its entirety.

BACKGROUND OF THE INVENTION

Field of the Invention

The invention relates to a method for determining the auditory threshold of a test subject. Furthermore, the invention relates to a method for setting hearing aid parameters of a hearing aid. In addition, the invention relates to a hearing aid system.

Hearing aids are generally used to reproduce sound signals to the sense of hearing of a user of the respective hearing aid. For this purpose, hearing aids contain at least one output transducer, typically a loudspeaker (also: "receiver"). In the form of so-called hearing aid devices, hearing aids are used to supply persons having impaired hearing ability with sound signals. Hearing aid devices regularly contain for this purpose at least one microphone, a signal processor for typically user-specific, frequency-dependent filtering, amplification, and/or damping of noises acquired by means of the microphone, and the above-mentioned output transducer. Depending on the type of the hearing impairment, the output transducer, in addition to the above-described loudspeaker, can also be configured as a bone vibrator or cochlear implant for mechanical or electrical stimulation of the sense of hearing of the user. In addition to the hearing aid devices, however, headphones, headsets, "hearables" and the like also fall under the concept of "hearing aid".

To individually adapt the signal processing in the signal processor, a so-called audiogram of the user is typically prepared. The so-called auditory threshold, i.e. from which volume value the user can hear a tone of a specific tone frequency, can be read out or determined therefrom. Firstly, tones of rising or at least changed tone frequency are typically presented in succession to the user for this purpose, wherein the volume increases in its value (continuously or step-by-step). However, this test method is comparatively susceptible to error, since the user frequently expects, within a time period after test beginning or confirmation of a preceding tone, to have a further tone of changed tone frequency presented and can thus confirm the tone "blind", i.e. without actually hearing the tone. On the other hand, this test method is comparatively simple.

BRIEF SUMMARY OF THE INVENTION

The invention is based on the object of enabling the most robust possible determination of the auditory threshold.

This object is achieved according to the invention by a method having the features of the first independent method claim. Furthermore, this object is achieved according to the invention by a computer program product having the features of the independent computer program product claim and by a method having the features of second independent method claim. Moreover, this object is achieved according to the invention by a hearing aid system having the features of the independent hearing aid system claim. Advantageous embodiments and refinements of the invention, which are partially inventive as such, are depicted in the dependent claims and the following description.

The method according to the invention is used to determine the auditory threshold of a test subject. "Auditory threshold" is understood here in particular as the lowest value of the volume (or also: of the level) of an acoustic signal, in particular of a noise (for example a tone), at which the test subject can still perceive, i.e. hear this noise. The auditory threshold is thus in particular frequency-dependent.

In the scope of the method according to the invention, multiple tone sets are presented in succession by means of an output transducer to a test subject, which tone sets predominantly contain a plurality of noises, in particular each having properties remaining uniform within a tone set but preferably at least partially differing from one another. After each presentation of one of these tone sets, the test subject is asked to indicate a perceived number of noises from this (i.e. in particular the immediately preceding) presented tone set. As a function of the perceived number of noises, at least for the presentation of the following tone set, a property of at least a part of the noises (in this following tone set) is changed in relation to the preceding tone set. This changed, following tone set is then presented to the test subject. As a function of the respective perceived number of tones in the presented tone sets (in particular at least two, preferably more than two), at least one value—in particular a single, preferably frequency-specific value and/or a curve over multiple tone frequencies—of the auditory threshold of the test subject is estimated.

In other words, a tone set having multiple noises (in particular having properties differing from one another but each remaining uniform as such) is performed for the test subject. For this tone set, the test subject has to make an indication about the perceived number of noises contained therein. As a function of the properties of the noises selected for the first tone set, a first estimated value for the auditory threshold may possibly already be estimated, in particular if the test subject has not heard all noises presented in the context of this tone set (i.e. has indicated them to be audible). For verification and/or more precise determination of the estimated value of the auditory threshold, at least one further tone set is then presented, for the noises of which the properties are at least partially changed. In particular for the case in which all noises are indicated as heard by the test subject in the first tone set or possibly also immediately following tone sets, a (first) estimated value is expediently not yet set for the auditory threshold.

The presentation of multiple tone sets having "predominantly a plurality of noises" is understood here and in the following in particular to mean that in principle the tone sets contain multiple noises which are played back or are to be played back, but also isolated tone sets can be provided having only one noise—in the extreme case even without noise. The number of such "single tone sets" or "empty tone sets" is low in relation to the total number of the tone sets and is, for example, in the range of up to 20%.

The term "noise" is understood here and in the following in particular as a suitable test noise, which differs from a typical "everyday noise" or "ambient noise" recorded as a "pure sample" (for example bird twitters, noise of an electrical appliance; which thus has in particular unknown properties with respect to its individual components) by way of predetermined and preferably clearly bounded properties. The noise is preferably a synthetically generated ("designed") noise or also a noise sample which is processed after a recording (for example by filtering undesired frequency components or the like). In a "broad" sense, the noise thus approximately represents a tone in particular in the musical meaning. This tone (or the noise) can be formed here, for example by a "pure" sine tone, a modulated sine tone, a sound (in the acoustic meaning; thus, for example also a chord), a so-called wobble tone, a so-called narrowband noise, or comparable sound signals. Frequency ranges from approximately one third up to one octave are preferably used for the above-described noises, in particular for the narrowband noise. Such noises (for example also a wobble tone or the like) can in principle have a varying, for example fluctuating frequency, but since this "moves" in a known and also in particular clearly bounded range (for example the frequency range indicated for the narrowband noise), the noise thus remains the same as such, this is also preferably understood here and in the following as a uniform property. In the following, the term "tone" is used as an equivalent term for "noise" for easier understanding—without excluding the specific designs of the tone as a sine tone, narrowband noise, etc. Accordingly, the term "tone set" is used here and in the following for a set which, as described above, can usually contain multiple tones, but in the extreme case even one tone or no tone at all.

The tones of a tone set are preferably presented in chronological succession, possibly separated by a time gap (or "pause") during the presentation of this tone set.

A loudspeaker is preferably used as an output transducer. I.e., the tone sets, specifically the tones thereof, are thus in particular acoustically presented. In principle, however, the method according to the invention may also be carried out using the output of the respective tone set by means of a bone vibrator or a cochlear implant.

The test subject preferably does not receive any information about the number of tones contained in the respective tone set.

The "following" tone set, which is changed as a function of the response to the (for example first) "preceding" tone set is optionally the actually immediately following one. Alternatively, this changed following tone set can also be presented following offset by an "interposed" tone set (for example already selected in its tones in parallel to the preceding tone set). The term "following" thus describes here and in the following in particular the tone set changed as a function of the corresponding preceding tone set.

Because the test subject has to indicate a number of tones and does not have to react only to the perception of a tone as such, the risk that the test subject—unintentionally or also intentionally to improve a result—will make a false indication is reduced. Since the selection of the corresponding following tone set is adapted as a function of the indications given, a test system is also more difficult to estimate for the test subject—for example in comparison to the tones presented in succession in increasing volume in the context of a classical audiogram. Therefore, better test results are to be expected in a comparatively simple way.

In one preferred method variant, a different volume value is assigned to each tone within the respective tone set as a property. That is to say, tones of different loudness are presented within a tone set. If the test subject indicates a reduced number of perceived tones from the actually presented number of tones in this case, it can thus be concluded that the tone having the lowest volume value was not audible to the test subject (i.e. was "too soft"). For example, in one tone set (selected at the beginning of the method, i.e. "first"), three tones having volume values of 40, 45, and 50 dB HL (dB "Hearing Level"; this dimensional unit is related in particular to the auditory threshold of a person with normal hearing) are presented. In this example, if the test subject indicates having heard two tones, it can be presumed that the tone at 40 dB HL was not audible.

In one expedient refinement of the method variant described immediately above, for particularly simple, frequency-dependent determination of the auditory threshold (specifically its frequency-specific value) of at least a first subset of the tone sets, the same tone frequency (in particular in the case of a sine tone) or, with respect to the alternatives described above, for example modulated sine tone, sound, narrowband noise etc., an equal frequency range (which, for example, symmetrically encloses the tone frequency to be studied) is assigned to the tones of each tone set of this first subset as a property. In other words, in multiple, preferably successively presented tone sets, the same tones are always presented, only having a different volume value. Thus, firstly for the present tone frequency (or the present frequency range), the value of the corresponding, frequency-specific auditory threshold can be determined in a simple manner. Preferably, the value of the auditory threshold is then determined for another tone frequency (or another frequency range) by means of a second subset, in particular in the context of a further pass having multiple tone sets. The three tones presented in the above-described exemplary embodiment are presented in this case, for example (for a first frequency-specific value of the auditory threshold) at (or in the range around) 2000 Hz. If the frequency-specific value of the auditory threshold is determined, a comparable sequence is preferably started for a further tone frequency (or a further frequency range).

In a further expedient method variant, in particular for the case that the tone frequency (or the frequency range) of the tones remains the same, the volume value of at least a part of the tones is changed for the presentation of the following tone set as property.

In a refinement of the above method variant, the volume value of at least this part of the tones (in particular of the following tone set) is preferably selected as a function of an estimated value, which is selected (or derived) from the number of perceived ("heard") tones of the preceding tone set or the preceding tone sets. In particular a value in the range of the "loudest" tone of the unheard tones up to the next-louder, still heard tone, for example the volume value of this next-louder tone is preferably assumed as the (first, "rough") estimated value for the auditory threshold. This volume value therefore corresponds to the lowest volume value which is contained in the number of tones indicated as audible. Thus, if three tones (preferably of uniform tone frequency or of the same frequency range)—in a continuation of the above-described exemplary embodiment, for example having volume values of 40, 45, and 50 dB HL—are presented and the test subject indicates having heard two tones, the estimated value for the auditory threshold is assumed in the case of the tone having middle volume value (thus at 45 dB HL here). In the following (possibly immediately following) tone set, for example, then three tones are presented at 35, 40, and 45 dB HL. If the test subject hereupon indicates only ("still") having heard one tone, the auditory threshold is highly probably at 45 dB HL. The volume values 45, 50, and 55 dB HL can also be presented (in this tone set or additionally in the scope of a further tone set). If the test subject indicates having heard three tones, the probability of the auditory threshold at 45 dB HL is also increased.

In one expedient method variant, the step width of the volume values between the individual tones of a tone set is selected consistently between the individual tone sets. That is to say, in all presented tone sets, the interval of the individual volume values in relation to one another is equal.

In an alternative variant, for more precise bounding of the value of the auditory threshold, the step width between the volume values is also changed, however. For example, after the presentation of the volume values 40, 45, and 50 dB HL and the specification that two tones were heard, the volume values are set to 42, 44, and 45 dB HL.

In an optional method variant, a different tone frequency (or a different frequency range) is respectively assigned as a property to each tone within the respective tone set. For example, in this case—at least within a tone set or over a subset of the tone sets—a constant volume value is selected for the tones. In this case, the tone frequency (or the frequency range) is thus varied at equal volume in order to find out the respective frequency-specific auditory threshold values. Alternatively, both tone frequency (or frequency range) and also volume are varied. In the latter case, a combinatorial evaluation and/or an experimental plan which is more complex in comparison to a property which remains constant are required.

In one preferred method variant, the volume value is established as the auditory threshold (specifically as the value of the auditory threshold) for a tone frequency which, in particular in more than 50% of the tone sets from each of which an estimated value for the auditory threshold can be derived (in which thus preferably neither all tones nor no tone were indicated as audible), was however able to be interpreted as ("still") audible (thus as an estimated value) in at least two tone sets, i.e. in particular which could be derived from the specifications of the test subject as the lowest audible volume value. In terms of the above-described exemplary embodiment, the volume value 45 dB HL is thus set as the value of the auditory threshold if, in the following tone set, which contains the volume values 35, 40, and 45 dB HL, one audible tone is indicated on the part of the test subject.

In one advantageous method variant, a tone is selected for a part of the tone sets which has a volume value below a volume value audible (in every case) at least to the test subject. However, the volume value is preferably selected for this tone in such a way that the tone is independently inaudible by the test subject, i.e. is preferably below a volume value audible to persons without hearing impairment (the auditory threshold for persons having normal hearing is typically at 0 dB HL, which also approximately corresponds to 3 dB SPL at 1000 Hz; in this method variant the volume value is preferably set to −10 dB HL "to be sure"). Such a tone set is preferably alternated with a "normal" tone set (i.e., one which has volume values at least potentially audible by the test subject). A check for so-called "false positive" responses is thus advantageously enabled. For the case in which the test subject indicates all tones as audible even with such a tone set, in particular multiple times, for example, a warning or an error essage is output. This variant is simple to implement in particular with respect to an automation of the method described here and in the following, since only the volume value has to be changed.

In an alternative (or optionally additional) method variant, the number of the included tones is also varied between the respective tone sets. "Overindications" of tones (i.e. a higher number of perceived tones than presented tones) also enable here an inference that the test subject makes "false" indications. It is also conceivable here that, isolated for this control, tone sets having only one reproduced tone or in the extreme case also without tone—or possibly a tone inaudible at least for the test subject and preferably for a person having normal hearing—and preferably a total tone set duration which is similar to a tone set having multiple tones are also presented.

To further increase the lack of susceptibility to errors, in one expedient method variant, a chronological duration of the individual tones is varied within one tone set and/or between the tone sets.

Additionally or alternatively, the chronological duration of gaps ("pauses") between the individual tones is varied. The probability is reduced by this chronological variation that the test subject will successfully attempt to estimate the duration of a tone set and to conclude the included number of tones therefrom, for example.

Furthermore, the sequence of the tones, in particular of the volume values (possibly also the tone frequencies) is also varied within a tone set and preferably also between the tone sets. In other words, not only is a decreasing (i.e. falling) or increasing sequence provided, but rather also a mixed one (for example volume values in the sequence 55, 45, and 50 dB HL).

In a further optional method variant, tone sets which have already been presented once are also presented repeatedly, in particular at an interval—i.e. after multiple other tone sets. The precision of the estimation of the value of the auditory threshold can thus be further increased.

In particular for the case that no tones are indicated as audible in one tone set, at least one tone having a volume value increased by, for example, 5 dB in relation to the highest volume value of the preceding tone set is output in the following tone set.

For the case in which all tones of a tone set are indicated as audible, in the next tone set a tone is preferably output which contains a volume value less by, for example, 10 dB than the lowest volume value of the preceding tone set.

For the case that the highest volume value (in particular tolerable to persons having normal hearing or also the maximum one which can be output) is indicated as inaudible (preferably twice), the method here and in the following is preferably continued with a new subset of tone sets having tones of a different tone frequency.

Before the actual determination of the auditory threshold, i.e. in particular before the selection of the first tone set, an acclimatization phase is expediently carried out. In this case—in particular for the case in which the same tone frequency or the same frequency range (in terms of a modulated tone, sound, or narrowband noise) is used for all tones—the tone used for the following tone sets, in particular for the following subset of tone sets, is played to the test subject. The test subject can thus acclimate themselves to the following test.

In one preferred method variant, the tone sets are presented by means of the output transducer, in particular a loudspeaker of a hearing aid, preferably a hearing aid device.

In one expedient method variant, the output transducer, in particular the above loudspeaker of the hearing aid and the query of the test subject, and in particular also the above-described change of the following tone set, i.e. at least the corresponding part of its tones, are controlled by a separate control unit. In other words, the control (or also: "processing") of the above-described method is thus preferably carried out by this control unit. The control unit is preferably a mobile terminal, preferably a smartphone, a tablet, or the like having an executable installed software application (app), which, upon execution on the mobile terminal, trains it to preferably automatically carry out the above-described method. In particular, the control unit contains for this purpose a microprocessor having a data memory on which the above-mentioned app is stored. In intended operation, the microprocessor processes commands which are contained in the program code of the app and thus carries out the above-described method.

The computer program product according to the invention thus preferably forms the above app and therefore has program code having commands which, upon the execution of the program code by a processor, specifically the above microprocessor, cause it to execute the above-described method, in particular automatically.

The method according to the invention for setting hearing aid parameters of a hearing aid of a test subject, specifically the above-described hearing aid, preferably hearing aid device, contains the above-described method for determining the auditory threshold of the test subject. In addition, after determining the auditory threshold, specifically its value, preferably the curve of the auditory threshold over multiple tone frequencies, signal processing algorithms of the hearing aid are adapted on the basis of the auditory threshold. The functionality for setting the hearing aid parameters is preferably also included in the above-described app.

The hearing aid system according to the invention contains at least the hearing aid and is configured to carry out the above-described method to determine the auditory threshold of the test subject, preferably automatically, at least partially in interaction with the test subject. The hearing aid system preferably contains the above-described mobile terminal for this purpose. The hearing aid system according to the invention is thus configured, in particular under control of the terminal, to present multiple tone sets in succession to the test subject by means of the output transducer, in particular the hearing aid, which tone sets predominantly contain a plurality of noises, in particular having properties which each remain the same within a tone set but are preferably at least partially different from one another. The hearing aid system is additionally configured to ask the test subject, after each presentation of one of these tone sets, to indicate a perceived number of noises from this presented tone set (i.e. in particular the immediately preceding tone set), and, as a function of the perceived number of noises, to change a property of at least a part of the noises (in this following tone set) in relation to the preceding tone set at least for the presentation of the following tone set. Furthermore, the hearing aid system is configured to then present this changed, following tone set to the test subject and, as a function of the respective perceived number of tones in the presented tone sets (in particular at least two, preferably more than two), to estimate at least one value—in particular a single, preferably frequency-specific value and/or a curve over multiple tone frequencies—of the auditory threshold of the test subject.

The hearing aid system and the above-mentioned method according to the invention (and also the computer program product upon execution by the processor) therefore share the same advantages and the physical features resulting from the respective descriptions.

The conjunction "and/or" is to be understood here and in the following in particular to mean that the features linked by means of this conjunction can be formed both jointly (e.g. a and b together) and also alternatively singularly (a alone or b alone).

Other features which are considered as characteristic for the invention are set forth in the appended claims.

Although the invention is illustrated and described herein as embodied in a method for determining the auditory threshold of a test subject, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Parts corresponding to one another are always provided with the same reference signs in all figures.

Figure 1:
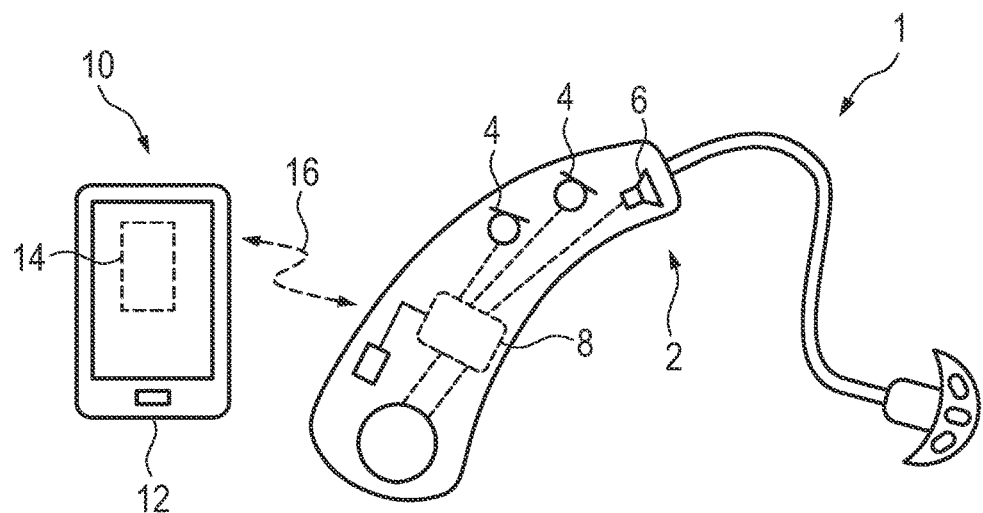
FIG. 1 is a schematic illustration of a hearing aid system.

Referring now to the figures of the drawings in detail and first, particularly to FIG. 1 thereof, there is shown a hearing aid system 1, which is configured and provided for the treatment of a person having impaired hearing. The hearing aid system 1 contains a hearing aid 2, which is configured as a hearing aid device, in the present exemplary embodiment as a hearing aid device to be worn behind the ear. The hearing aid 2 has in this case as electronic components two microphones 4, a loudspeaker 6 as an output transducer, and a signal processor 8. In intended operation, the microphones 4 acquire ambient noises and relay them in the form of electrical microphone signals to the signal processor 8. Signal processing algorithms run on the latter, the parameters of which enable an adaptation of the hearing aid 2 to the type and severity of the hearing impairment of the person, specifically reflect them in intended operation. For example, frequency-specific amplification values are predetermined by the parameters, in particular to boost microphone signals, the volume value of which is below a value of an auditory threshold of the person, and thus to make them audible to the person (also referred to as "hearing aid wearer"). The processed microphone signals are subsequently output via the loudspeaker 6.

Figure 2:
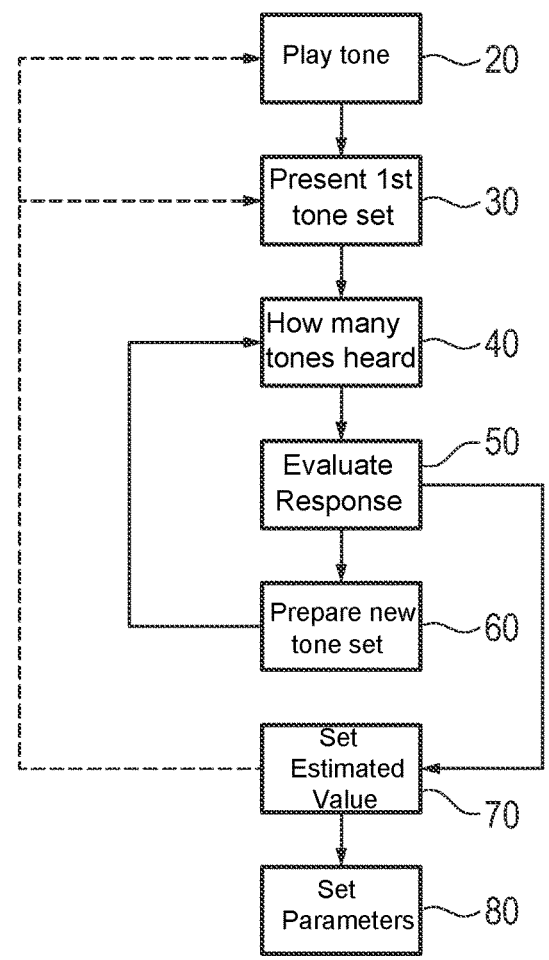
FIG. 2 is a flow chart of a method carried out by the hearing aid system.

An audiogram of the person is regularly prepared for the determination of the correct parameters. For automated preparation of the audiogram, the hearing aid system 1 has a control unit 10, which is configured to carry out, in interaction with the person, a method described in greater detail in the following on the basis of FIG. 2. The control unit 10 is specifically formed by a mobile terminal, in particular a smartphone 12, on which control software (also: "computer program product", but abbreviated hereinafter: "app 14") is installed so it is executable. In intended operation, the smartphone 12 is in wireless communication connection 16 with the hearing aid 2.

In a first method step 20 (see FIG. 2), a tone, in the present exemplary embodiment a pure sine tone, having a specific tone frequency, specifically and by way of example 2000 Hz here, is played to the person—in this case representing a test subject. If the person hears this (sine) tone, the test for determining the frequency-specific values of the auditory threshold of the person can begin. Method step 20 represents an acclimatization phase.

Alternatively to the pure sine tone, a modulated sine tone, a sound, or narrowband noise having a frequency range from approximately one third up to one octave can also be used.

In a second method step 30, a first tone set having three tones of different volume values, for example 60, 50, and 55 dB HL, is compiled by the control unit and presented, i.e. played, to the person via the loudspeaker 6 of the hearing aid 2. The individual tones are each separated from one another by a pause.

In a following method step 40, the person is asked—specifically a corresponding question is displayed on the smartphone 12, optionally also spoken—how many tones the person could hear.

In a further method step 50, the response of the person, who has input this on the smartphone 12, is evaluated and three new tones (having the same tone frequency) having partially changed volume values are compiled for a further tone set. For the case in which the person indicates having heard three tones, three new tones are compiled, the loudest volume value of which is 10 dB softer than the softest one of the preceding tone set (in the present exemplary embodiment thus 45, 40, and 35 dB HL). These tones are presented in the scope of a further tone set in a following method step 60. In contrast, if none of the tones is heard, three tones having changed volume values are again offered in method step 60, wherein the volume values are louder by at least 5 dB than the loudest volume value of the preceding tone set, thus here 65, 70, and 75 dB HL.

If at least one tone is not perceived in the first or one of the following tone sets, the volume values are sorted by increasing value and the number of unheard tones is "deleted" beginning with the lowest volume value. The lowest "remaining" volume value is set as the estimated value for the auditory threshold here. If thus, for example, in the case of a presentation of three tones having the volume values 50, 55, and 60 dB HL, it is indicated on the part of the person that two tones were heard (which thus corresponds to one unperceived tone), the estimated value is thus set to 55 dB HL. For the case in which all included tones or no tones are indicated as heard in the first or an immediately following tone set—expressed the other way around—initially an estimated value is also not set for the auditory threshold.

The pauses (i.e. time gaps) between the individual tones and the tone lengths themselves are varied here within and between the tone sets.

After method step 60, the sequence returns to method step 40, the response of the person is obtained and evaluated in method step 50.

If, upon repeated presentation of the volume value corresponding to the estimated value of the auditory threshold, this is also indicated as the lowest audible volume value repeatedly—for more than 50% with respect to the number of the presentations of this one volume value—the sequence passes to a final method step 70 and this estimated value is set as the ("final" or "confirmed") value of the auditory threshold. In other words, if more than 50% of all presentations of tone sets which contain at least one tone having equal volume value, this volume value was determined as the lowest audible value (and thus used as the estimated value), just this volume value is set in method step 70 as the value of the auditory threshold. Subsequently, the sequence jumps back to method step 20 or 30 and the same method is carried out again using a new tone frequency.

If the value of the auditory threshold has been determined for every tone frequency, for example in steps of 500, 1000, 2000, 3000 to 4000 Hz, the parameters are set/predetermined again on this basis in a further method step 80 and sent to the hearing aid 2.

The subject matter of the invention is not restricted to the above-described exemplary embodiments. Rather, further embodiments of the invention can be derived by a person skilled in the art from the above description. In particular, the individual features of the invention and its design variants described on the basis of the various exemplary embodiments can also be combined with one another in another way.

The following is a summary list of reference numerals and the corresponding structure used in the above description of the invention:

1 hearing aid system
2 hearing aid
4 microphone
6 loudspeaker
8 signal processor
10 control unit
12 smartphone
14 app
16 communication connection
20 method step
30 method step
40 method step
50 method step
60 method step
70 method step
80 method step

The invention claimed is:

1. A method for setting hearing aid parameters of a hearing aid for a test subject, which comprises the steps of:
   determining an auditory threshold of the test subject by the performing the substeps of:
      presenting multiple tone sets, which predominantly contain a plurality of tones, in succession to the test subject by an output transducer of the hearing aid, the output transducer being a loudspeaker, a bone conduction receiver, or a cochlear implant;
      asking the test subject to indicate a perceived number of tones from a presented tone set after each presentation of one of the multiple tone sets;
      changing a plurality of properties of the plurality of tones in the multiple tone sets in dependence on the perceived number of tones, the plurality of properties being changed in relation to a preceding tone set for a presentation of a following tone set and presenting the following tone set to the test subject as one of the multiple tone sets;
      estimating at least one value of the auditory threshold of the test subject in dependence on the perceived number of tones in the multiple tone sets that were presented;
      controlling, by a separate control unit, the output transducer, the presenting step, the asking step, and the changing of the plurality of properties in the changing step, wherein the separate control unit performs the asking step; and subsequently adapting a parameter of a signal processing algorithm configured to run on a signal processor of the hearing aid based on the at least one value of the auditory threshold to thereby adapt the hearing aid to a hearing impairment of the test subject;

wherein the parameter of the signal processing algorithm determines a frequency-specific amplification value to boost a microphone signal having a volume level below the at least one value of the auditory threshold;

wherein the plurality of properties that are changed in the changing step are selected from the group consisting of a first set of properties, a second set of properties, a third set of properties, and a fourth set of properties;

wherein the first set of properties includes a time duration of individual tones, a time duration of gaps between individual tones, an order of volume values, and a number of tones contained in one of the multiple tone sets with respect to a number of tones contained in another one of the multiple tone sets;

wherein the second set of properties includes the time duration of individual tones, the order of volume values, and the number of tones contained in one of the multiple tone sets with respect to the number of tones contained in another one of the multiple tone sets;

wherein the third set of properties includes the time duration of gaps between individual tones, the order of volume values, and the number of tones contained in one of the multiple tone sets with respect to the number of tones contained in another one of the multiple tone sets; and wherein the fourth set of properties includes the time duration of individual tones, the duration of gaps between individual tones, and the order of volume values.

2. The method according to claim 1, wherein a different volume value is assigned to each of the plurality of tones within a respective tone set of the multiple tone sets.

3. The method according to claim 2, wherein for a frequency-dependent determination of the auditory threshold of at least one first subset of the multiple tone sets, a same tone frequency or a same frequency range is assigned to the plurality of tones of each tone set of the multiple tone sets of the first subset as the property.

4. The method according to claim 2, wherein the plurality of properties that are changed in the changing step include a volume value of at least some of the plurality of tones.

5. The method according to claim 4, wherein the volume value of at least a part of the plurality of tones is selected in dependence on the estimated at least one value of the auditory threshold selected from a number of the plurality of tones perceived from at least the preceding tone set.

6. The method according to claim 2, wherein a step width of the different volume value assigned to each of the plurality of tones is equal.

7. The method according to claim 2, wherein the different volume value is established as the auditory threshold for a tone frequency which was indicated as audible by the test subject for more than 50% of ones of the multiple tone sets for which neither all tones were indicated as audible nor no tones were indicated as audible by the test subject.

8. The method according to claim 2, wherein a part of the multiple tone sets contains a tone having the volume value which is below 0 Db HL.

9. The method according to claim 1, wherein a different tone frequency or a different frequency range is respectively assigned as one of the plurality of properties to each noise within a respective tone set of the multiple tone sets.

10. The method according to claim 1, which further comprises varying the time duration of the individual tones and/or of gaps between the individual tones within one of the multiple tone sets and/or between the multiple tone sets.

11. The method according to claim 1, wherein the output transducer is the loudspeaker and the loudspeaker is part of a hearing aid.

12. The method according to claim 1, wherein the plurality of tones have properties that remain uniform within a tone set.

13. The method according to claim 1, wherein the separate control unit is a mobile terminal having an executable installed app.

14. The method according to claim 1, wherein the at least one value of the auditory threshold of the test subject is estimated by setting the at least one value of the auditory threshold of the test subject to a lowest volume value of the perceived number of tones.

15. The method according to claim 1, wherein the separate control unit performs the asking step by displaying at least one question.

* * * * *